(12) United States Patent
Hammann et al.

(10) Patent No.: US 9,358,636 B2
(45) Date of Patent: Jun. 7, 2016

(54) LASER PROCESSING MACHINE

(75) Inventors: Gerhard Hammann, Korntal-Muenchingen (DE); Ulrich Ritter, Aystetten (DE); Dirk Fey, Neewiller (FR); Giovanni Sanfelici, Karlsruhe (DE); Gunther Krieg, Karlsruhe (DE)

(73) Assignee: TRUMPF Werkzeugmaschinen GmbH + Co. KG, Ditzingen (DE)

( * ) Notice: Subject to any disclaimer, the term of this patent is extended or adjusted under 35 U.S.C. 154(b) by 0 days.

(21) Appl. No.: 12/972,665

(22) Filed: Dec. 20, 2010

(65) Prior Publication Data

US 2011/0220626 A1    Sep. 15, 2011

Related U.S. Application Data

(63) Continuation of application No. PCT/EP2008/004983, filed on Jun. 20, 2008.

(51) Int. Cl.
| | |
|---|---|
| *B23K 26/02* | (2014.01) |
| *B23K 26/03* | (2006.01) |
| *B23K 26/08* | (2014.01) |
| *B23K 26/12* | (2014.01) |
| *B23K 26/38* | (2014.01) |

(Continued)

(52) U.S. Cl.
CPC .............. *B23K 26/03* (2013.01); *B23K 26/0884* (2013.01); *B23K 26/12* (2013.01); *B23K 26/128* (2013.01); *B23K 26/38* (2013.01); *G01N 21/1702* (2013.01); *G01N 29/14* (2013.01); *G01N 29/46* (2013.01); *B23K 2201/18* (2013.01)

(58) Field of Classification Search
USPC ............... 219/121.6, 121.61, 121.83, 121.66, 219/121.67
See application file for complete search history.

(56) References Cited

U.S. PATENT DOCUMENTS

| | | | |
|---|---|---|---|
| 4,381,148 A * | 4/1983 | Ulrich .................... | G01J 5/42 356/213 |
| 4,504,717 A | 3/1985 | Arai | |

(Continued)

FOREIGN PATENT DOCUMENTS

| | | | |
|---|---|---|---|
| DE | 19535720 A1 | | 3/1997 |
| DE | 10200349 | * | 7/2003 |

(Continued)

OTHER PUBLICATIONS

Translation of the International Preliminary Report on Patentability for corresponding PCT Application No. PCT/EP2008/004983, mailed Jan. 27, 2011, 13 pages.

(Continued)

*Primary Examiner* — Dana Ross
*Assistant Examiner* — Ayub Maye
(74) *Attorney, Agent, or Firm* — Fish & Richardson P.C.

(57) ABSTRACT

A laser processing machine for processing workpieces includes a beam guide containing a gas atmosphere, and also includes an apparatus for investigating the gas atmosphere in the beam guide for impurities. The investigation apparatus makes use of the photoacoustic effect. The measuring apparatus has a measuring chamber and at least one measuring head, where the beam guide acts as the measuring chamber. As a measuring chamber, the beam guide contains the gas atmosphere that is to be investigated and also a modulated laser beam modulated. The measuring head(s) are integrated into the beam guide and are used to detect the photoacoustic effect in the measuring chamber.

3 Claims, 3 Drawing Sheets

(51) Int. Cl.
*G01N 21/17* (2006.01)
*G01N 29/14* (2006.01)
*G01N 29/46* (2006.01)

(56) References Cited

U.S. PATENT DOCUMENTS

| | | | | |
|---|---|---|---|---|
| 4,504,727 | A * | 3/1985 | Melcher | B23K 26/03 219/121.62 |
| 4,594,004 | A * | 6/1986 | Ishida | G01N 21/1702 356/433 |
| 4,817,413 | A * | 4/1989 | Asano | G01N 21/1702 73/24.02 |
| 5,454,347 | A * | 10/1995 | Shibata et al. | 117/202 |
| 5,673,114 | A * | 9/1997 | Ushio | 356/432 |
| 5,705,816 | A * | 1/1998 | Ronge | G01N 21/39 250/343 |
| 5,811,753 | A * | 9/1998 | Weick | B23K 26/123 219/121.67 |
| 6,873,414 | B2 * | 3/2005 | Schuth et al. | 356/432 |
| 6,894,248 | B2 * | 5/2005 | Arakawa | B23K 26/03 219/121.67 |
| 7,595,463 | B2 | 9/2009 | Weick et al. | |
| 8,212,176 | B2 * | 7/2012 | Akiyama et al. | 219/121.67 |
| 8,258,430 | B2 * | 9/2012 | Weick et al. | 219/121.83 |
| 2001/0026354 | A1 | 10/2001 | Aoki | |
| 2004/0094525 | A1 * | 5/2004 | Weick et al. | 219/121.83 |
| 2005/0061778 | A1 * | 3/2005 | Arakawa et al. | 219/121.6 |
| 2005/0263509 | A1 * | 12/2005 | Yamazaki et al. | 219/121.84 |
| 2010/0116797 | A1 * | 5/2010 | Weick et al. | 219/121.67 |

FOREIGN PATENT DOCUMENTS

| | | |
|---|---|---|
| DE | 10200349 A1 | 7/2003 |
| DE | 102005033408 A1 | 8/2006 |
| EP | 0749800 A2 | 12/1996 |
| EP | 1386690 A1 | 2/2004 |
| EP | 1463929 A1 | 10/2004 |
| JP | 5212575 A | 8/1993 |
| JP | 2008527323 A | 7/2008 |
| WO | 9533594 A1 | 12/1995 |
| WO | 2007004168 A1 | 1/2007 |

OTHER PUBLICATIONS

International Search Report from corresponding PCT Application No. PCT/EP2008/004983, mailed Mar. 20, 2009, 2 pages.

\* cited by examiner

LASER PROCESSING MACHINE

CROSS REFERENCE TO RELATED APPLICATION

This application is a continuation of, and claims priority under 35 U.S.C. §120 to PCT/EP2008/004983, filed on Jun. 20, 2008, and designating the U.S., which is hereby incorporated by reference in its entirety.

TECHNICAL FIELD

This disclosure relates to a laser processing machine for processing workpieces.

BACKGROUND

In a laser processing machine having a $CO_2$ laser, the laser radiation for processing the material is generated by molecular vibrations. The generated laser radiation is usually guided through a gas atmosphere which, by appropriate measures, is kept free of substances that are capable of absorbing the generated laser radiation.

$CO_2$ laser radiation can be absorbed by various molecules. A precondition for absorption is that one of the molecular bonds has the appropriate binding energy. Examples of such gaseous substances that should be kept away from the beam are $SF_6$, $C_2H_4$, halogenated hydrocarbons, ammonia, alcohols, acetone, and $CO_2$.

At a general level, the detrimental effect of those gases resides in the absorption itself and in an associated attenuation of the laser radiation power required for processing. Moreover, the optical effects on the laser radiation resulting from the absorption can include widening of the beam and a distortion of the beam phase front. An increase in temperature and the ensuing change in the refractive index of the medium through which the beam passes also can have an adverse effect on the laser radiation.

Studies have shown that an impurity of less than 100 ppb (0.1 ppm) $SF_6$ is sufficient to cause impairment of the cutting of a sheet of steel at 3 kW laser power. $SF_6$, with a wavelength of 10 μm, exhibits very high beam absorption.

SUMMARY

With the aid of the photoacoustic effect it is possible to detect impurities in the beam guide of a laser processing machine. A discussion of the photoacoustic effect can be found in "Laser opto-acoustic spectroscopy—A new technique of gas analysis", Anal. Chem. 46 239A, 1974, which is incorporated herein by reference in its entirety. The measurement method is based on the fact that the interaction of a modulated electromagnetic wave with certain molecules produces sound which can be measured using a microphone.

A laser processing machine is disclosed in European Patent Application No. EP 1 386 690 A1 and in German Patent Application No. DE 102 00 349 A1, where it is proposed that part of the laser radiation provided for laser processing be decoupled and passed into a separate measuring cell in which the gas to be analyzed can be investigated for impurities with the aid of the photoacoustic effect.

German Patent Application No. DE 10 2005 033 408 A1 and US Patent Application Publication No. 2001/0026354 A1 relate to exposure systems with which structures are applied to a substrate by exposure. There is provided for that purpose a light source, preferably a laser, from which light is radiated towards the substrate. Between the light source and the substrate, a mask provided with the structure to be applied is arranged on the light source side and an optical projection system is arranged on the substrate side. The optical projection system includes a housing and a plurality of optical lenses arranged in the interior thereof. The housing of the optical projection system is flushed with gas to remove impurities which would otherwise impair the functioning of the optical projection system. Apparatuses for investigating the composition of the flushing gas stream may be arranged either in the interior of or outside the housing of the optical projection system. The photoacoustic effect is not used by the foregoing apparatuses.

International patent application publication WO 2007/004168 A1 discloses a photoacoustic spectrometer that can be used for the detection of impurities in air samples.

A method and an arrangement for testing the leak-tightness of housings is disclosed in German Patent Publication No. DE 195 35 720 A1, where an escaping gas is illuminated by a light beam of a matching light source such that, if there is a leak in the housing, the photoacoustic effect can be measured. For improving the measurement, a feedback loop is proposed.

To adjust the gas atmosphere in beam guides a molecular sieve can be used (see, for example, European Patent Publication No. EP 0 749 800 A1) or nitrogen can be employed as a flushing gas for the beam guide (see, for example, International Patent Publication No. WO 95/33594 A1).

Shields against the ingress of gas from the outside can also be used.

The present disclosure is related to simplifying the monitoring of the gas atmosphere and of all the operating gases of the beam guide that interact with the laser processing. A laser processing machine is disclosed, that has a beam guide being provided as a measuring chamber and is operable to contain a power-modulated laser beam. A measuring head is integrated into the beam guide. An in situ gas sensor system for beam guiding systems based on photoacoustics also is disclosed. The laser processing machine enables direct detection of relevant impurities of the gas atmosphere in the beam guide. In contrast to other techniques, the beam guide is itself the measuring chamber. The laser generator generates not only the laser beam for workpiece processing but also the measuring beam for the photoacoustic measurement to be carried out. Consequently, a separate beam source for generating the measuring beam is not required. The photoacoustic measurement can be carried out during processing of the workpiece, but also can be carried out during periods when a workpiece is not being processed. Photoacoustic measurement during workpiece processing is possible if the workpiece is processed using a power-modulated laser beam. For example, power-modulated laser beams can be used to pierce metal sheets. Periods when the workpiece is not being processed include, for example, periods during which the drives of the laser processing machine are being lubricated and/or during which adjustments are being made to the clearance control. The clearance control serves to maintain a defined distance between the laser processing head and the workpiece to be processed. When measurement is carried out during a period when the workpiece is not being processed, the laser processing head through which the laser beam exits into the working area may be moved, especially under numerical control, to a defined position in which it cooperates with a device for absorption of the measuring beam. As beam absorbers it is possible to use, among other things, devices of the kind that are already commonly used as safety devices and which, as such, serve to intercept laser beams and convert the beam power into heat which is to be dissipated by the beam absorber. Such beam absorbers are currently used, for example, at the output mirror of laser resonators.

Implemented in a technically simple manner, the at least one measuring head forms, together with a control and evaluation unit connected to the laser generator of the laser processing machine, a system for investigating the gas atmosphere in the beam guide. If the control and evaluation unit is used to modulate the laser power, it is possible for different types of impurities to be monitored.

Preferably, the control and evaluation unit is in communication with the machine controller of the laser processing machine. If high levels of impurities are detected, the machine controller is able to react accordingly, for example, by shutting down the laser processing. It is also possible to trigger a flushing operation if a level of contamination of the gas atmosphere in the beam guide is determined to be in excess of a specified limit. During the flushing operation, the beam guiding chamber is flushed with gas of a desired composition. Under those circumstances, permanent flushing on a reduced scale compared with conventional permanent flushing of the beam guide is sufficient to provide a gas atmosphere of the desired composition in the beam guiding chamber of the laser processing machine. In some implementations, permanent flushing of the beam guide is no longer necessary.

For sound detection, at least one measuring head may be built into the beam guide, e.g., provided in the interior of the beam guide or disposed in a window of the beam guide. Both alternatives make possible a direct measurement of the photoacoustic effect in the beam guide used as the measuring chamber. In cases where the beam guide is provided with a venting and pressure-relief valve, the measuring head can be arranged in the immediate vicinity of the mentioned valve. With such an arrangement of the measuring head, the measured photoacoustic effect is a particularly reliable reflection of the actual conditions in the gas atmosphere of the beam guide.

With a view to a simple configuration of the measuring arrangement, at least one measuring head in the form of a simple microphone is used. Alternatively, or additionally, microphone arrays including multiple microphones can be used.

In general, in one aspect, the disclosure features a laser processing machine for processing workpieces that includes a laser beam guide operable to contain a gas atmosphere and a laser beam, and a photoacoustic sensor system operable to analyze the gas atmosphere in the beam guide for impurities, the photoacoustic sensor system including a measuring chamber and at least one measuring head operable to detect a photoacoustic effect in the measuring chamber, in which at least a portion of the beam guide forms the measuring chamber, and the beam guide includes the at least one measuring head.

Implementations of the laser processing machine can include one or more of the following features. The laser processing machine can include a laser generator, in which the photoacoustic sensor system includes a control and evaluation unit connected to the laser generator. The control and evaluation unit can be operable to modulate the laser output. The laser processing machine can further include a machine controller, in which the control and evaluation unit is operable to communicate with the machine controller.

In some implementations, the at least one measuring head is built into the beam guide.

In some implementations, the at least one measuring head is in a window of the beam guide.

In some implementations, the at least one measuring head includes a microphone.

The details of one or more embodiments are set forth in the accompanying drawings and the description below. Other features and advantages will be apparent from the description and drawings, and from the claims.

DETAILED DESCRIPTION

Figure 1:
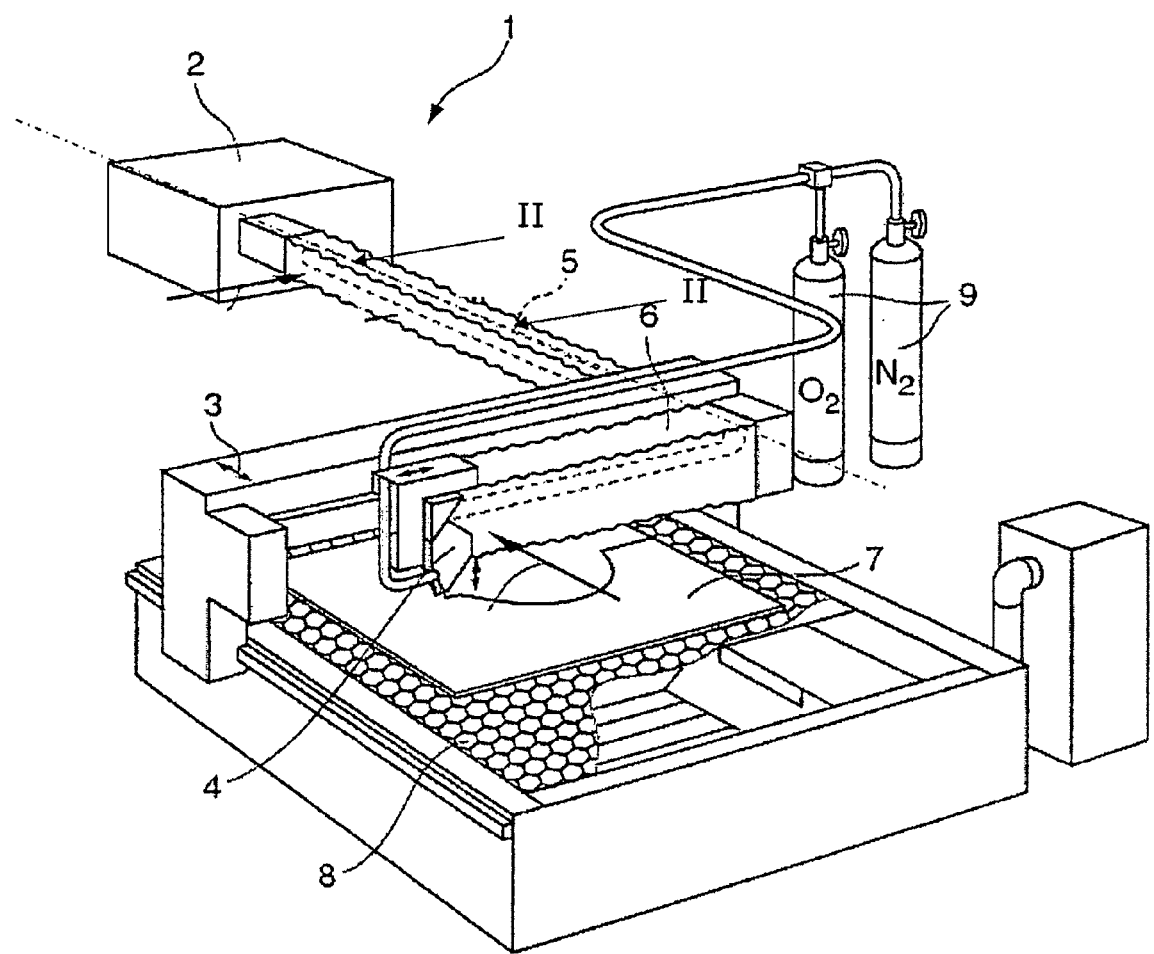
FIG. 1 is a three-dimensional illustration of an exemplary laser processing machine.

As shown in FIG. 1, an exemplary laser processing machine 1 includes a laser generator 2 ($CO_2$ laser) and a laser processing head 4 which is movable relative thereto in the direction of the double-headed arrow 3. A laser beam 5 generated by means of the laser generator 2 is passed from the laser generator 2 through a beam guiding chamber 6 flushed with a gas and serving as a beam guide to the processing head 4. The laser beam 5 is directed onto a workpiece 7 to be processed, where the workpiece 7 is in the form of a metal sheet placed on a workpiece support 8 of the laser processing machine 1.

Both piercing and laser cutting are assisted by addition of a gas. Oxygen, nitrogen, compressed air and/or any application-specific gases may be used as cutting gases 9. The gas that is ultimately used may depend on the materials being cut and on the required quality of the workpiece. Cutting gas is delivered in the processing head in the vicinity of the processing location.

The beam guiding chamber 6 is substantially filled with pure gas, e.g., nitrogen. The beam guiding chamber 6 may be delimited by a bellows or some other kind of hermetic closure such as, but not limited to, a tube or telescopic tube. The laser beam 5 is diverted and focused inside the laser processing head 4, so that a focused laser beam is directed onto the workpiece 7.

Figure 2:
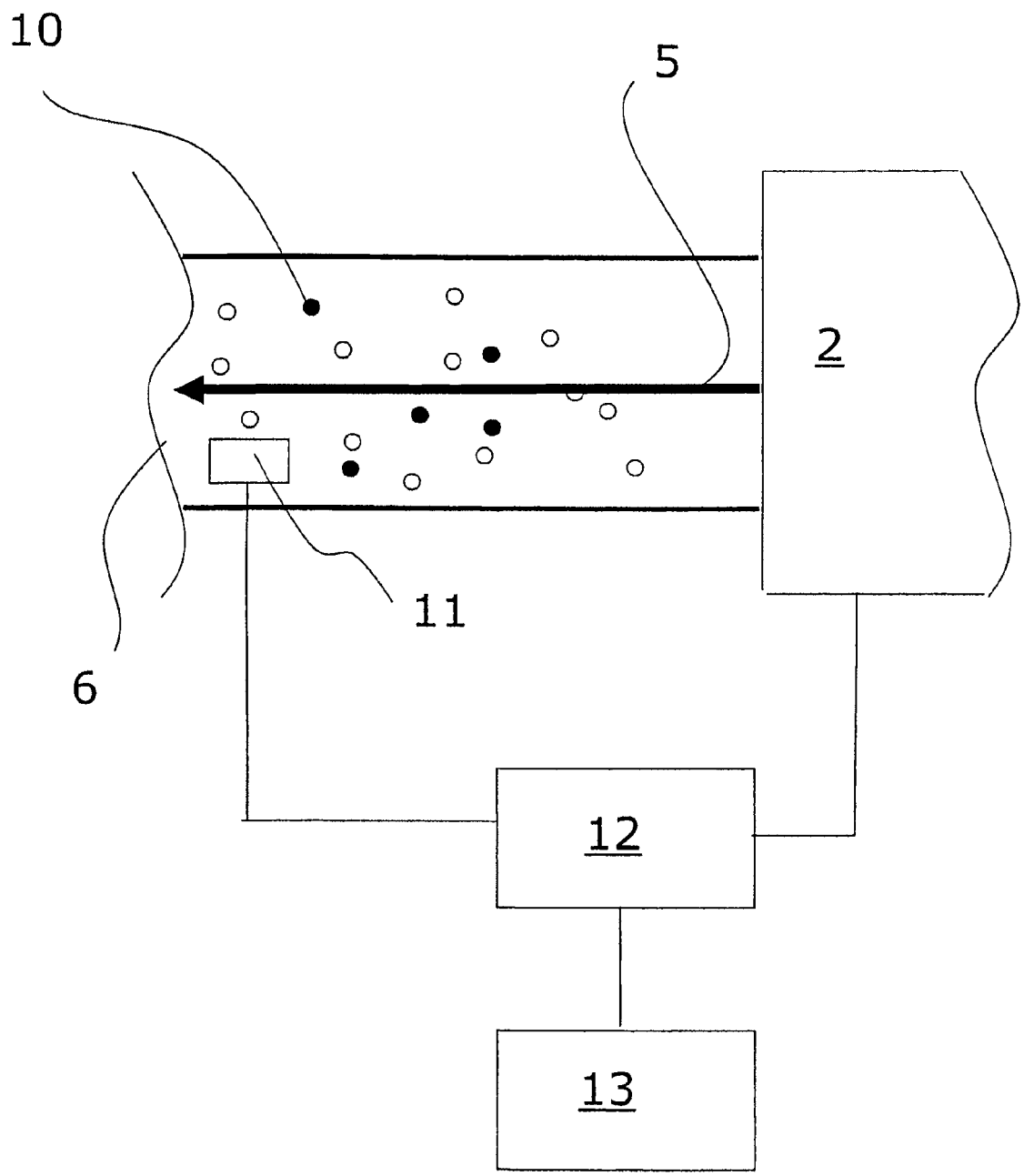
FIG. 2 is a schematic diagram illustrating an enlarged detail of a first exemplary construction of a beam guide of the laser processing machine shown in FIG. 1.
Figure 3:
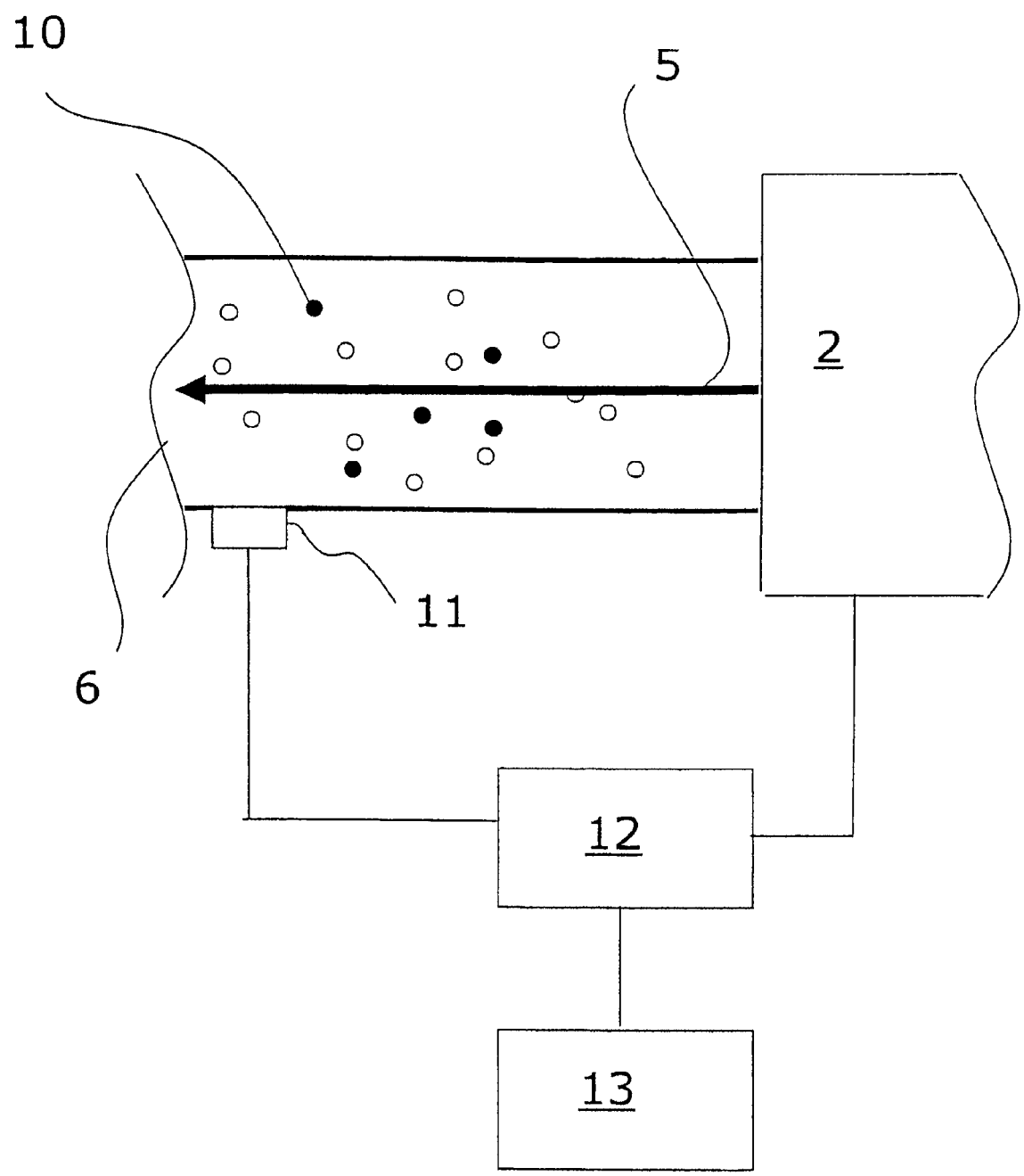
FIG. 3 is a schematic diagram illustrating an enlarged detail of a second exemplary construction of a beam guide of the laser processing machine shown in FIG. 1.

As illustrated in FIGS. 2 and 3, the laser beam 5 may interact with certain molecules 10 in the beam guiding chamber 6. That may lead to power absorption and, in some implementations, to a widening of the laser beam 5. Changes in the focusing conditions may, in turn, have a direct effect on the processing result in the case of laser cutting.

Accordingly, beam guiding systems are encapsulated and are flushed with purified compressed air or inert gas (e.g., nitrogen or $CO_2$-free compressed air), which can lead to a significant increase in operating costs. However, in some implementations, contaminated flushing gases may be inadvertently delivered to the beam guiding chamber 6 or interfering gases may enter the chamber 6 through leaks. In general, the impurities are not recognized and finding the reason for the impurities can be costly.

An apparatus for analyzing the gas atmosphere to identify impurities in the beam guiding chamber 6 is provided. The apparatus utilizes the photoacoustic effect and the beam guiding chamber 6 is used as a measuring chamber. The apparatus for investigating the gas atmosphere in the beam guiding chamber 6 can include a sensor system which directly detects a degree of contamination of the gas atmosphere in the beam guiding chamber 6. The sensor system substantially includes a measuring head 11 for sound such as, for example, a microphone, and a control and evaluation unit 12, which is in communication with both the laser generator 2 and a machine controller 13.

Various safety, control and/or operating measures of the machine controller 13 can occur in response to a signal of the control and evaluation unit 12. For example, the machine controller 13 may generate a warning for the operator of the laser processing machine 1. Depending on the degree of contamination of the beam guiding chamber 6, automatic shutdown of the laser processing machine 1 is also possible. Alternatively, compensatory measures may be initiated including, for example, an increase in the quantity of flushing gas through the beam guiding chamber 6. The signal of the control and evaluation unit 12 may also be incorporated as part of a control loop to monitor the gas atmosphere in the beam guiding chamber 6.

The sensor system of the measuring arrangement may be disposed at one or more desired locations in the beam guiding chamber 6. For example, FIG. 2 shows the measuring head 11 disposed in the interior of the beam guiding chamber 6. In another example, FIG. 3 shows the measuring head 11 in a window of the beam guiding chamber 6.

The measurement may be carried out during processing of the workpiece, where the same laser beam that is used for workpiece processing can be used to produce the photoacoustic effect. Alternatively, the measurement can be carried out during a non-productive period. When the measurement is performed during the non-productive period, the laser generator may be put into an operating mode favorable for measuring the photoacoustic effect that occurs. In some implementations, a power modulation with a mark-to-space ratio of 1:1 at a pulsing frequency of 6 to 8 kHz has been found advantageous. The greater the maximum power (pulse amplitude), the stronger the measurement signal that can be produced.

To modulate the laser power, the control and evaluation unit 12 is used. If the power changes upon modulation are sufficiently great (e.g., greater than 1 kW), the excitation of the contaminant of the gas atmosphere in the beam guiding chamber 6 is so great that the sound can be measured directly at the beam guiding chamber 6. No separate measuring chamber is required. The contamination of the gas atmosphere in the beam guiding chamber 6 leads to a linear sound source along the laser beam 5.

One or more microphones or measuring heads 11 may be used to measure the sound output of the linear sound source.

The output signal of the measuring heads 11 is preferably considered in the frequency domain (for example, by digitizing the output signal and performing a Fourier transform). To obtain a differentiation between measuring effect and ambient noise, the signal is evaluated at the laser modulation frequency. The amplitude at that frequency corresponds to the degree of contamination.

A number of embodiments have been described. Other embodiments are within the scope of the following claims.

What is claimed is:

1. A laser processing machine for processing workpieces, the laser processing machine comprising: a laser generator configured to generate a laser beam and to modulate the power the laser beam for producing a photoacoustic effect; a laser processing head configured to focus the laser beam that has been generated and power modulated by the laser generator; and an investigation system for investigating a gas atmosphere in a measuring chamber for impurities based on the photoacoustic effect, the investigation system comprising the measuring chamber, a photoacoustic sensor system, and a control and evaluation unit, wherein the control and evaluation unit is connected to the laser generator and is operable to modulate an output of the laser generator such that the laser generator modulates the power of the laser beam for producing the photoacoustic effect, the measuring chamber is arranged between the laser generator and a laser beam focusing device inside the laser processing head, the measuring chamber being configured to contain a gas atmosphere and to guide the power modulated laser beam on a laser beam path from the laser generator to the laser processing head; the photoacoustic sensor system is configured to analyze the gas atmosphere in the measuring chamber for impurities based on the photoacoustic effect responsive to the power modulated laser beam, the photoacoustic sensor system comprising at least one measuring head built into the measuring chamber or arranged in a window of the measuring chamber and configured to detect the photoacoustic effect in the measuring chamber, wherein the measuring chamber comprises the at least one measuring head.

2. The laser processing machine according to claim 1, further comprising a machine controller, wherein the control and evaluation unit is operable to communicate with the machine controller.

3. The laser processing machine according to claim 1, wherein the at least one measuring head comprises a microphone.

* * * * *